US012544250B2

(12) United States Patent
Arsiwala

(10) Patent No.: US 12,544,250 B2
(45) Date of Patent: Feb. 10, 2026

(54) SPLINT FOR IMMOBILIZING A LIMB OF A USER

(71) Applicant: United States Government As Represented By The Department Of Veterans Affairs, Washington, DC (US)

(72) Inventor: Mohammed Ali Arsiwala, Northville, MI (US)

(73) Assignee: United States Government as represented by the Department of Veterans Affairs, Washington, DC (US)

( * ) Notice: Subject to any disclaimer, the term of this patent is extended or adjusted under 35 U.S.C. 154(b) by 281 days.

(21) Appl. No.: 18/350,934

(22) Filed: Jul. 12, 2023

(65) Prior Publication Data

US 2024/0016648 A1 Jan. 18, 2024

Related U.S. Application Data

(60) Provisional application No. 63/388,636, filed on Jul. 12, 2022.

(51) Int. Cl.
*A61F 5/058* (2006.01)

(52) U.S. Cl.
CPC ...... *A61F 5/05866* (2013.01); *A61F 5/05816* (2013.01)

(58) Field of Classification Search
CPC .............. A61F 5/05866; A61F 5/05816; A61F 5/0118; A61F 5/05858; A61F 5/05841; A61F 5/058; A61F 5/05; A61F 5/04; A61F 5/01; A61F 5/00; A61F 5/013; A61F 5/0102; A61F 5/0104
See application file for complete search history.

(56) References Cited

U.S. PATENT DOCUMENTS 7,942,840 B2 * 5/2011 Hargrave .............. A61F 13/108 602/5
2023/0099955 A1 * 3/2023 Deren ................. A61F 5/05816 602/21

FOREIGN PATENT DOCUMENTS

EP 3269338 A1 * 1/2018 ......... A61F 5/05816
WO WO-02071988 A1 * 9/2002 ......... A61F 5/05816

* cited by examiner

*Primary Examiner* — Tarla R Patel
(74) *Attorney, Agent, or Firm* — Ballard Spahr LLP

(57) ABSTRACT

A splint for use on a forearm, a wrist, and a hand of a user, including a rigid shell assembly with dorsal and a volar shell bodies, the dorsal and volar shell bodies each including a forearm portion, a wrist portion, and a hand portion. The dorsal and volar shell bodies are configured to releasably receive the forearm, wrist, and hand of the user therebetween. A dorsal compressible assembly and a volar compressible assembly extend along the inner surfaces of the dorsal and volar shell bodies, respectively. The volar compressible assembly includes an inflatable forearm bladder, an inflatable wrist bladder, and an inflatable hand bladder, each of which includes a valve to allow each of the inflatable bladders to be inflated independently of the other inflatable bladders.

17 Claims, 11 Drawing Sheets

SPLINT FOR IMMOBILIZING A LIMB OF A USER

CROSS-REFERENCE TO RELATED APPLICATION

This application claims priority to and the benefit of the filing date of U.S. Patent Application No. 63/388,636, filed Jul. 12, 2022, the entire disclosure of which is incorporated by reference herein.

FIELD

The application is generally related to medical devices and procedures and, more particularly, to splint devices and methods of use thereof that facilitate immobilizing the limb of a victim such as due to broken bones, sprains, and the like.

BACKGROUND

Existing splints for immobilizing injuries are often deficient with regard to several aspects. For instance, current splints may not provide customizable fitting for supporting the wrist, hand, and forearm of a patient. For example, although current splints may include a single adjustable bladder on a dorsal or volar side of a patient's arm, the single bladder does not allow for the customization of the splint to individual areas of the patient's arm while the patient wears the splint. Specifically, although a single bladder may extend from the hand to the forearm, the bladder does not allow one to increase pressure on the wrist while lowering pressure on the hand.

SUMMARY

Embodiments of the disclosed splint devices are configured to allow the rapid immobilization of a user's limb. Specifically, embodiments of the disclosed device allow on-site immobilization of the limb with a customizable fit by way of one or more inflatable bladders. An example embodiment of one such splint for use on a forearm, a wrist, and a hand of a user includes a rigid shell assembly having a dorsal shell body and a volar shell body, the dorsal shell body and the volar shell body each including a forearm portion, a wrist portion, and a hand portion. The dorsal shell body and the volar shell body are configured to releasably receive the arm, including forearm, the wrist, and the hand of the user, therebetween. A dorsal compressible assembly extends along an inner surface of the dorsal shell body and a volar compressible assembly extends along an inner surface of the volar shell body. One or both of the dorsal compressible assembly and the volar compressible assembly includes an inflatable forearm bladder adjacent the forearm portion, an inflatable wrist bladder adjacent the wrist portion, and an inflatable hand bladder adjacent the hand portion of the corresponding shell body. Each of the inflatable forearm bladder, the inflatable wrist bladder, and the inflatable hand bladder includes a valve to allow each of the inflatable bladders to be inflated independently of the other inflatable bladders.

In some embodiments, the present invention discloses splint for use on a limb of a user, the splint having a rigid shell assembly with a first shell body and a second shell body, wherein the first shell body and the second shell body are configured to releasably receive the limb of the user therebetween. A first compressible assembly extends along an inner surface of the first shell body, and a second compressible assembly extends along an inner surface of the second shell body, one or both of the first compressible assembly and the second compressible assembly including a first inflatable bladder and a second inflatable bladder. The first shell body is configured to receive a first side of the limb and the second shell body is configured to receive an opposite second side of the limb, and each of the inflatable bladders includes a valve to allow each of the first and the second inflatable bladders to be inflated independently of the other inflatable bladder.

Yet another embodiment of the present invention provides a method of immobilizing a limb of a user. The method includes the steps of providing a splint having a rigid shell assembly with a dorsal shell body and a volar shell body, the dorsal shell body and the volar shell body each including a forearm portion, a wrist portion, and a hand portion, wherein the dorsal shell body and the volar shell body are configured to releasably receive the forearm, the wrist, and the hand of the user therebetween. The splint also includes a dorsal compressible assembly extending along an inner surface of the dorsal shell body, and a volar compressible assembly extending along an inner surface of the volar shell body. The volar compressible assembly includes an inflatable forearm bladder adjacent the forearm portion, and an inflatable wrist bladder adjacent the wrist portion of the volar shell body. Further steps include positioning the splint on the user so that the inflatable forearm bladder and the inflatable wrist bladder are adjacent the forearm and the wrist of the user, inflating the inflatable forearm bladder to a first pressure, and inflating the inflatable wrist bladder to a second pressure, wherein the first pressure and the second pressure are not equal.

According to some embodiments, a splint for facilitating healing of various injuries may include an outer shell assembly and a plurality of inflatable bladders. The outer shell assembly may include an upper outer shell body and a lower outer shell body, and the upper outer shell body may include a first inner surface and a first outer surface. The lower outer shell body may include a second inner surface and a second outer surface. The upper outer shell body may be configured to be positioned against a dorsal side of the hand, and the lower outer shell body may be configured to be positioned against a volar side of the hand. The upper outer shell body is fastenable to the lower outer shell body using at least one fastening element after positioning the upper outer shell body on the dorsal side of the hand and positioning the lower outer shell body on the volar side of the hand. Further, the plurality of inflatable bladders may be inflated based on transferring at least one fluid in the plurality of inflatable bladders. The at least one fluid may include a gas, a liquid, etc. Preferably, the plurality of inflatable bladders may be attached to the first inner surface of the upper outer shell body, and the plurality of inflatable bladders may be attached to the second inner surface of the lower outer shell body. Further, the at least one valve may be disposed on the upper outer shell body and the lower outer shell body.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein.

DETAILED DESCRIPTION

Figure 1:
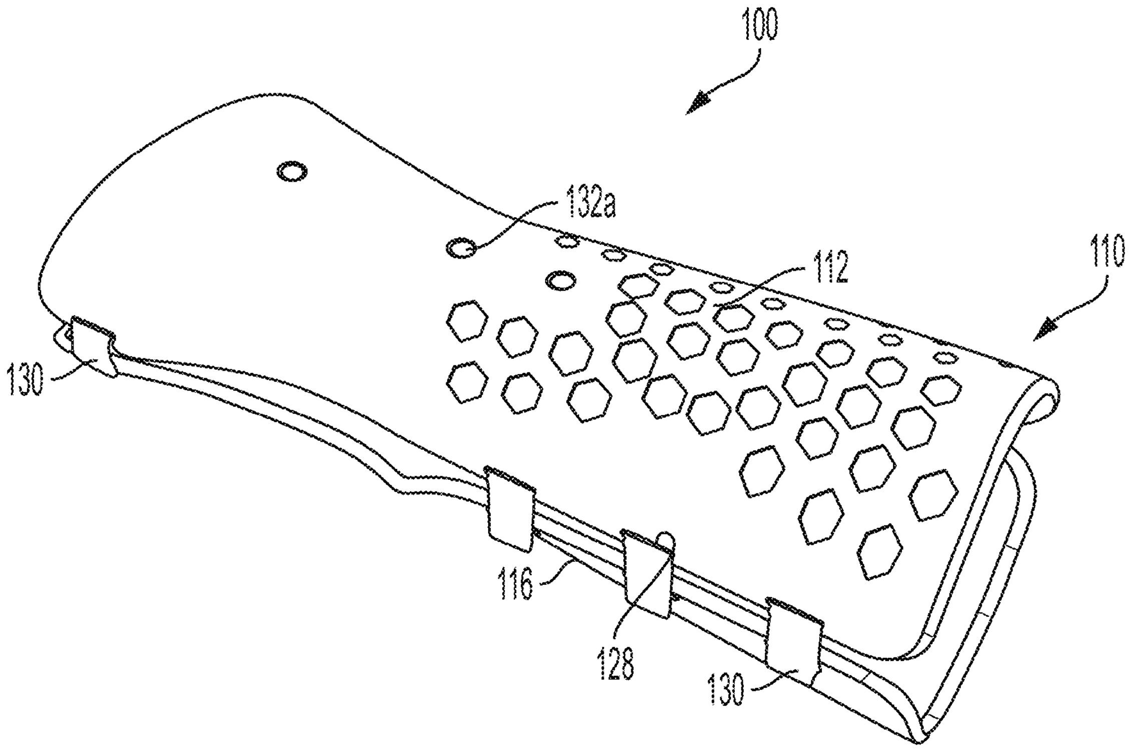
FIG. 1 is an isometric view of an embodiment of a splint device for immobilizing the limb of a user in accordance with an embodiment of the present invention.

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedents "about," "substantially," or "generally," it is contemplated that values within up to 15%, up to 10%, up to 5%, or up to 1% (above or below) of the particularly stated value can be included within the scope of those aspects. In other aspects, when angular values are approximated by use of the antecedents "about," "substantially," or "generally," it is contemplated that angular values within up to 15 degrees, up to 10 degrees, up to 5 degrees, or up to one degree (above or below) of the particularly stated angular value can be included within the scope of those aspects.

The word "or" as used herein means any one member of a particular list and, unless context dictates otherwise, in alternative embodiments, can also include any combination of members of that list.

In the following description and claims, wherever the word "comprise" or "include" is used, it is understood that the words "comprise" and "include" can optionally be replaced with the words "consists essentially of" or "consists of" to form another embodiment.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Figure 2A:
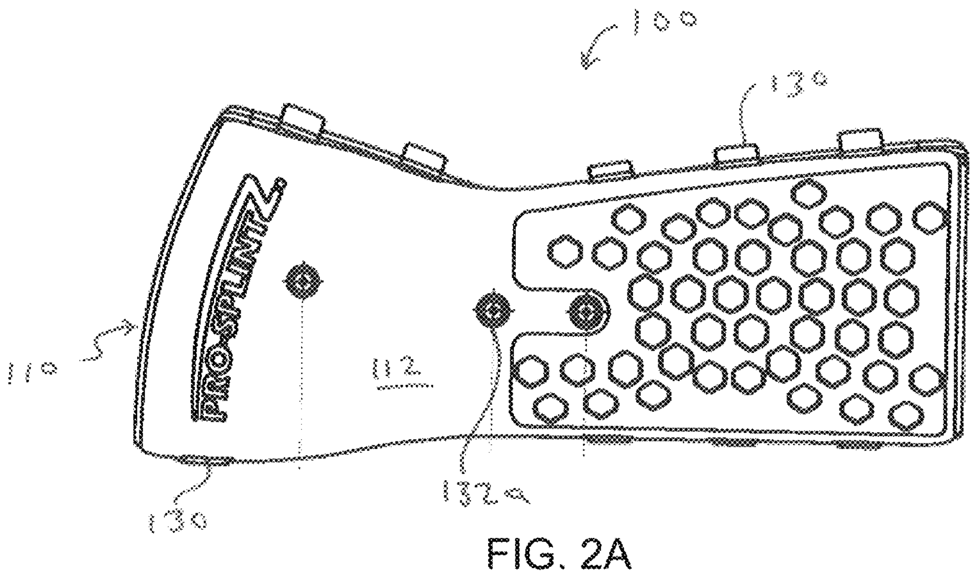
FIGS. 2A, 2B, and 2C are top, side, and bottom views, respectively, of the dorsal and volar rigid shell halves of the splint device shown in FIG. 1.
Figure 2B:
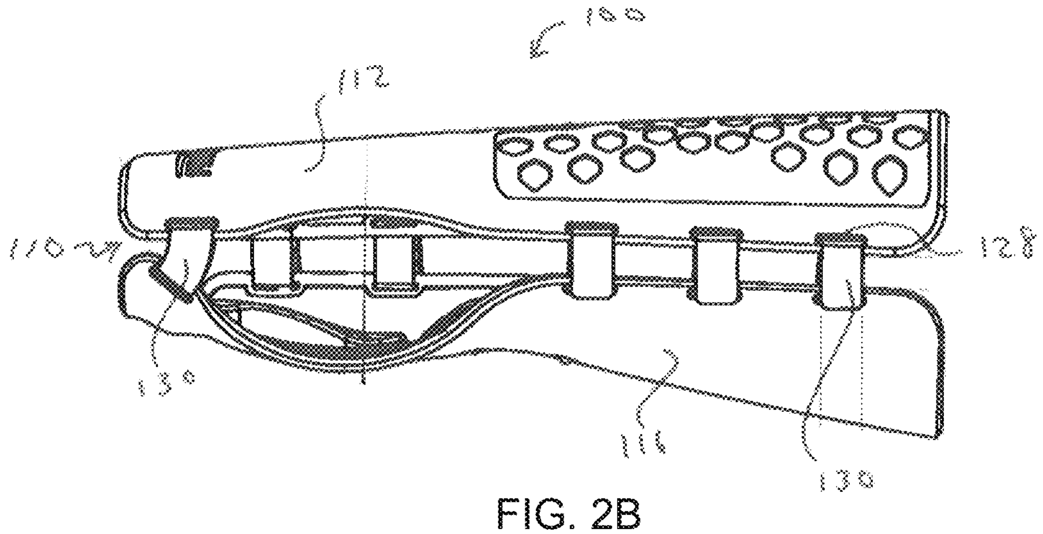
Figure 2C:
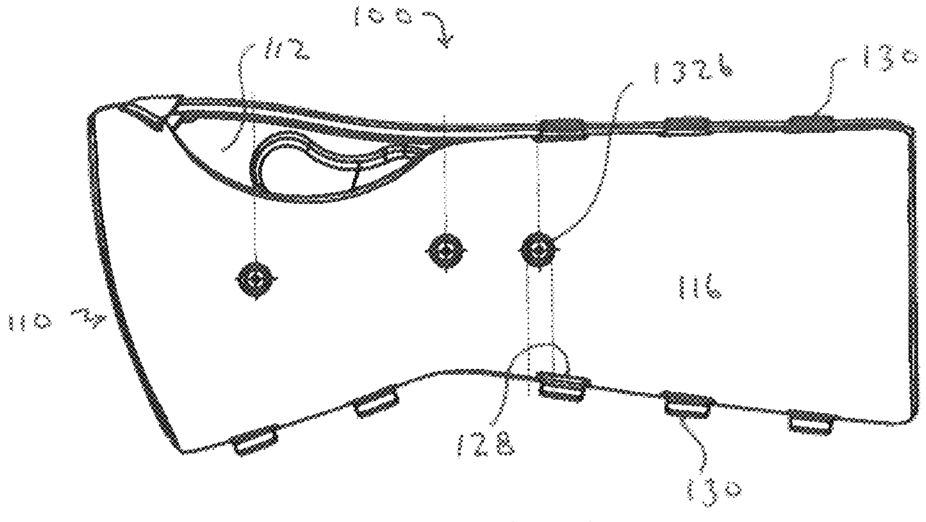
Figure 3:
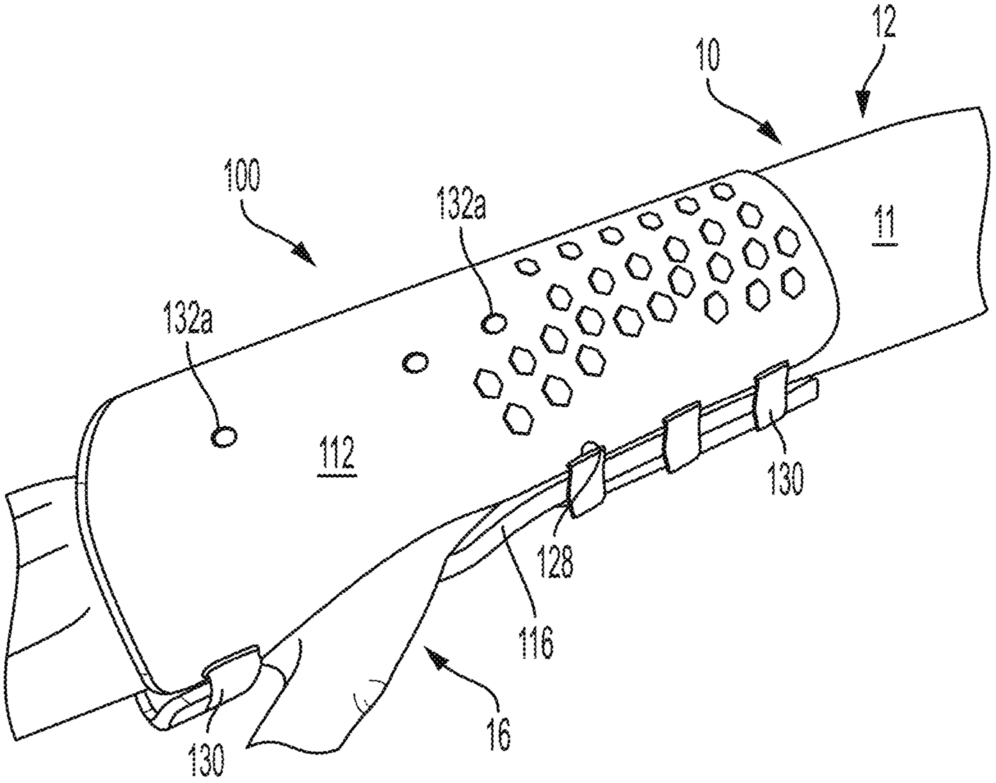
FIG. 3 is an isometric view of the splint device shown in FIG. 1, fitted on the arm of a user.
Figure 4A:
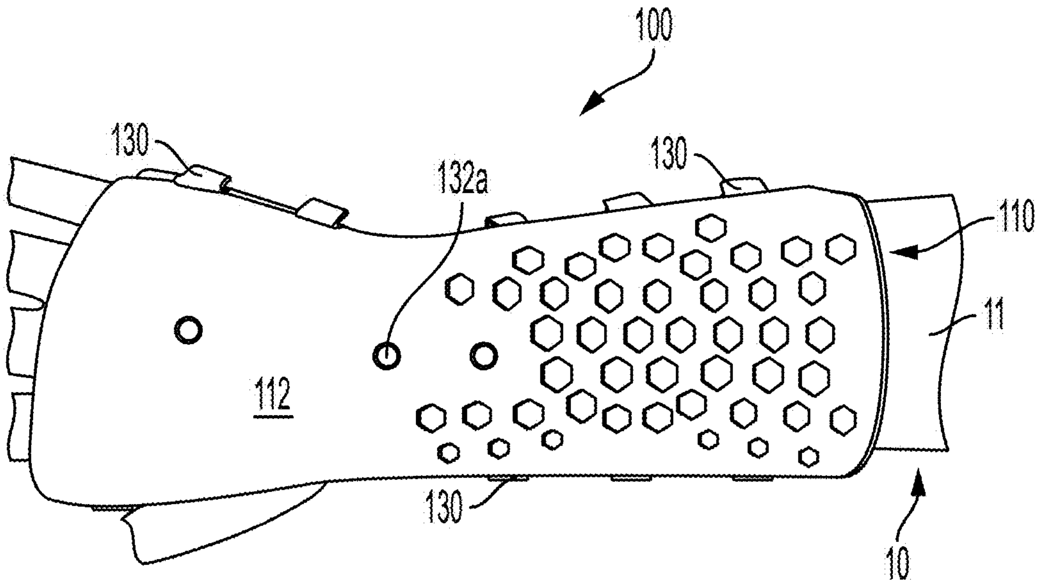
FIGS. 4A and 4B are a top plan view and bottom plan view, respectively, of the splint device on the arm of the user, as shown in FIG. 3.
Figure 4B:
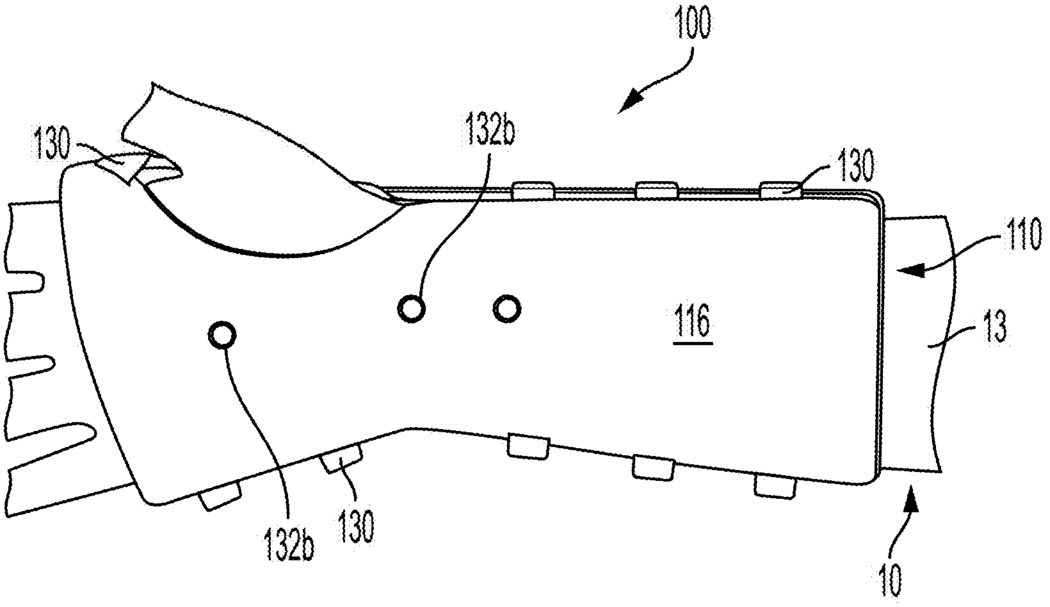

Referring now to FIGS. 1 through 3, an embodiment of a splint device 100 for immobilizing the arm 10 of a user in accordance with the invention is shown. Specifically, FIG. 1 shows a top perspective view of the assembled splint device 100 for immobilizing the right arm 10 of a user. The splint device 100 includes a rigid outer shell assembly 110 including an upper (dorsal) shell body 112 and a lower (volar) shell body 116. Preferably, as discussed in greater detail below, the dorsal and the volar shell bodies 112 and 116 include compressible assemblies 120*a* and 120*b*, respectively, that extend along their inner surfaces. Preferably, the dorsal and volar shell bodies 112 and 116 are adjustably secured to each other, and to the user's arm 10, by a plurality of adjustable straps 130 positioned along the edges thereof. Although adjustable straps 130 are disclosed, it is contemplated that other adjustable and/or elastic elements can be used to secure the dorsal and volar shell bodies 112 and 116 to each other.

Figure 5:
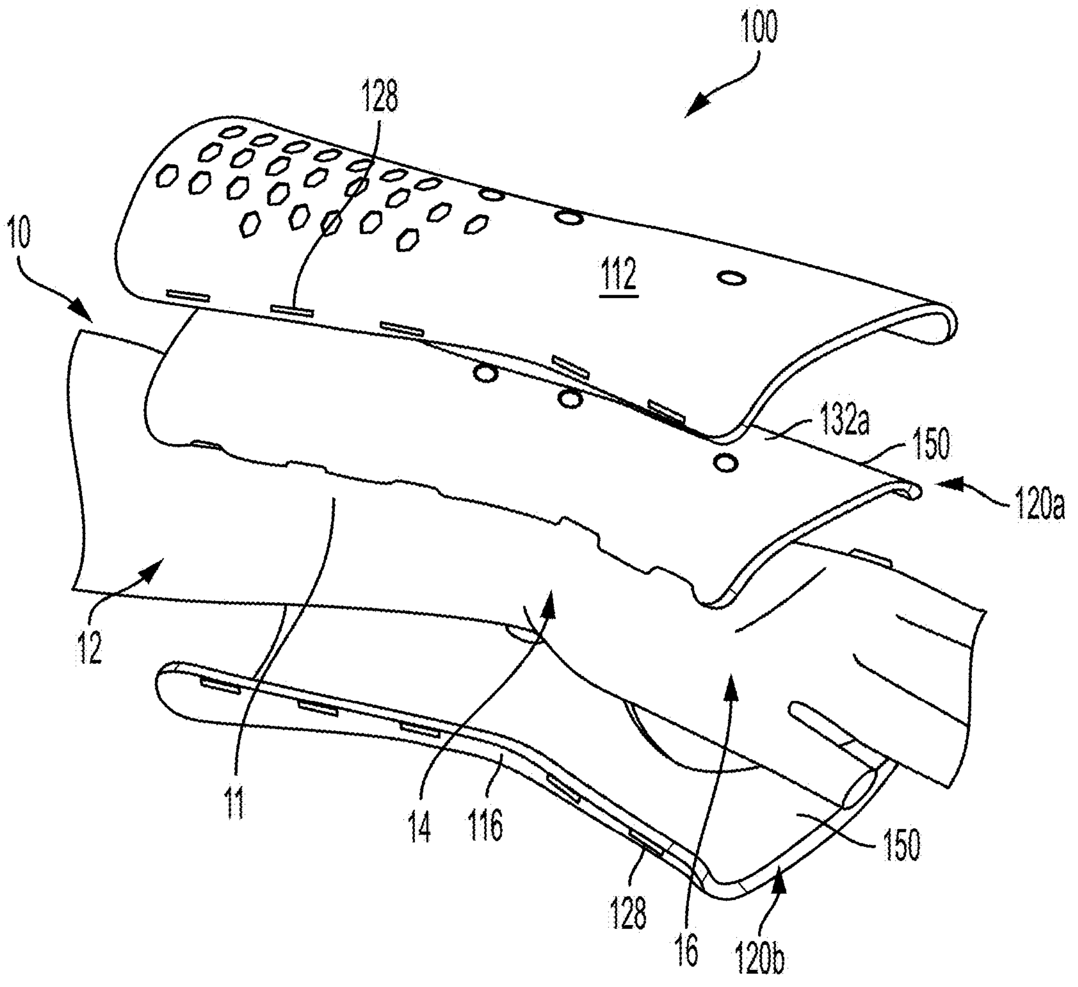
FIG. 5 is an exploded view of the splint device shown in FIG. 3.

As shown, the dorsal shell body 112 is configured to be received adjacent the dorsal surface 11 of the user's forearm 12, wrist 14, and hand 16, whereas the volar shell body 116 is configured to be received adjacent the volar surface 13 of the user's forearm 12, wrist 14, and hand 16. The dorsal and volar shell bodies 112 and 116 are constructed of a rigid material such as, but not limited to, polypropylene. As such, when the dorsal and volar shell bodies 112 and 116 are secured to the lower arm 10 of the user, the hand 16, wrist 14, and forearm 12 are immobilized with respect to each other. As best seen in FIG. 5, both the dorsal and volar shell bodies 112 and 116 include a plurality of slots 128 disposed lengthwise along their side edges. The slots 128 are configured to receive a plurality of adjustable straps 130, such as, but not limited to, hook-and-loop type fastener straps that allow the splint device 100 to accommodate variously sized arms therein. In other aspects, it is contemplated that the slots 128 can be configured to receive a plurality of elastic bands (or other elastic structures) that allow the splint device 100 to accommodate variously sized arms therein.

Figure 6A:
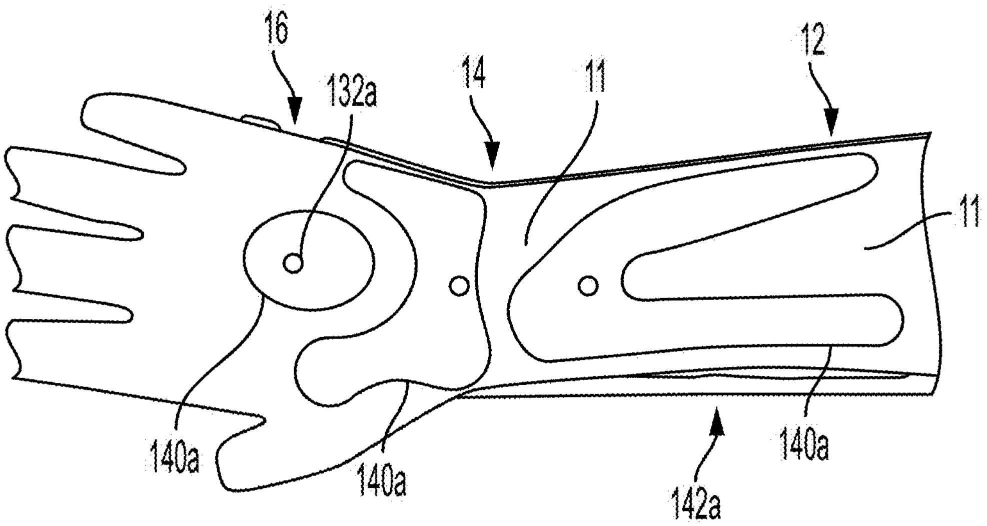
FIGS. 6A and 6B are volar and dorsal views respectively, of the arm of the user of the splint showing positioning of the volar and dorsal forearm, wrist, and hand inflatable bladders.
Figure 6B:
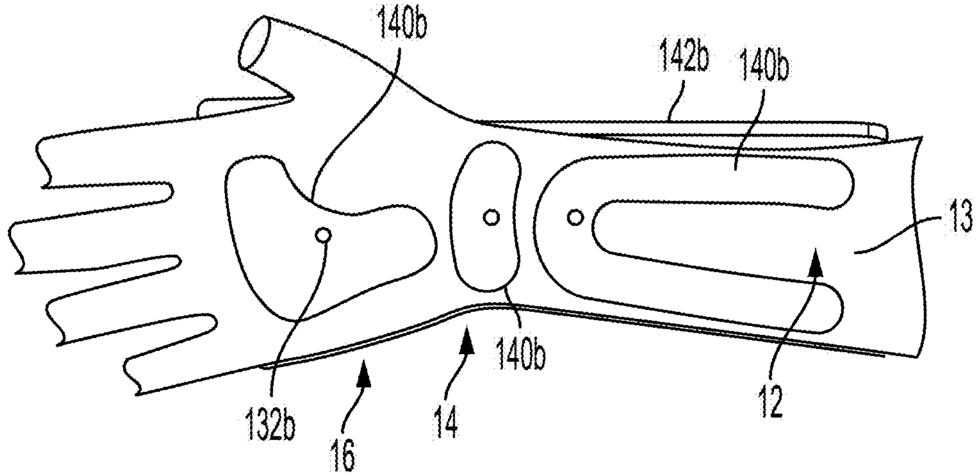

Referring to FIGS. 5, 6A, and 6B, the dorsal and volar shell bodies 112 and 116 include compressible assemblies 120*a* and 120*b*, respectively, secured to their inner surfaces. Preferably, both the dorsal and volar compressible assemblies 120*a* and 120*b* include an inflatable liner 142*a* and 142*b*, respectively, adhered directly to the inner surfaces thereof. Preferably, the inflatable liners 142*a* and 142*b* are constructed of a material such as, but not limited to, vinyl, and form one or more inflatable pockets, or bladders, 140*a* and 140*b*, respectively. Note, although the inflatable bladders of each shell assembly can be formed from a continuous liner 142*a*, 142*b*, each inflatable bladder is fluidly isolated from the other inflatable bladders and is inflatable independently of the other inflatable bladders. For example, referring specifically to FIG. 6A, the inflatable liner 142*a* of the dorsal compressible assembly 120*a* forms three inflatable bladders 140*a* that may each be inflated via its own inflation valve 132*a*. Similarly, inflatable liner 142*b* forms a plurality of independently inflatable bladders 140*b* that may each be inflated via its own inflation valve 132*b*. Preferably, the inflation valves 132*a* and 132*b* are of the type typically used with footballs, basketballs, etc., although other types of valves may be used. Although the bladders 140*a*, 140*b* can advantageously be formed from a continuous liner 142*a*, 142*b*, in alternative aspects, it is contemplated that each bladder 140*a*, 140*b* can be formed from a distinct liner that is separate from the liners that form the other bladders.

Still referring to FIGS. 6A and 6B, the dorsal and volar inflatable bladders 140*a* and 140*b* can be shaped and configured to fill the anatomical curvatures and contours due to the shape of the forearm 12, wrist 14, and hand 16 of the user. Specifically, by optimizing the shape of each of the inflatable bladders 140*a* and 140*b*, the splint device 100 is better able to accommodate for the gaps and voids in the outer surface of the user's arm due to bones, tendons, etc., that project outwardly as compared to the remainder of the user's arm. As such, the splint device 100 is better able to immobilize the user's arm in the vicinity of the injury, leading to reduced inflammation and pain. For example, based on the contours of a user's forearm 12, some preferred embodiments of the dorsal and volar inflatable bladders 140*a* and 140*b* adjacent the forearm may be substantially U-shaped with the bottom of the U-shape adjacent the more narrow wrist 14 and the elongated legs of the U-shape extending toward the user's elbow. At the narrower wrist 14 area, additional dorsal and volar inflatable bladders 140*a* and 140*b* may be used to fill the recessed portions between the forearm 12 and the hand 16 for added stability. Additionally, voids and depressions on the user's dorsal and volar sides of the hand 16 may be supported by an independent pair of bladders 140*a* and 140*b*. Although there may be similarities in arm shape amongst the arms of different users, the ability to inflate each bladder independently of the other bladders allows for customized fit not heretofore realized. In use, it is contemplated that the bladder configurations disclosed herein, which fill the anatomical curvature, contour, and shape of portions of the specific user's body, can support healing of bones, tendons, and ligaments of the surrounding joint structures by reducing inflammation and pain.

Although three inflatable bladders 140*a*, 140*b* for both the dorsal and volar compressible assemblies 120*a* and 120*b* are shown, alternate embodiments may include either fewer or more inflatable bladders 140*a*, 140*b*. Additionally, the number of inflatable bladders 140*a* in the dorsal compressible assembly 120*a* may differ from the number of inflatable bladders 140*b* in the volar compressible assembly 120*b*. Moreover, the shape of the inflatable bladders 140*a*, 140*b* may be altered as desired to facilitate variously sized arms and shapes of arms. As best seen in FIG. 5, a layer of compressible material 150 such as, but not limited to, memory foam, is preferably included in both the dorsal and volar compressible assemblies 120*a* and 120*b* between the inflatable liners 142*a* and 142*b* and the user's arm 10. The compressible foam 150 and a moisture wicking material disposed on top of the foam increases comfort and helps to fill in contours of the user's arm.

Figure 7:
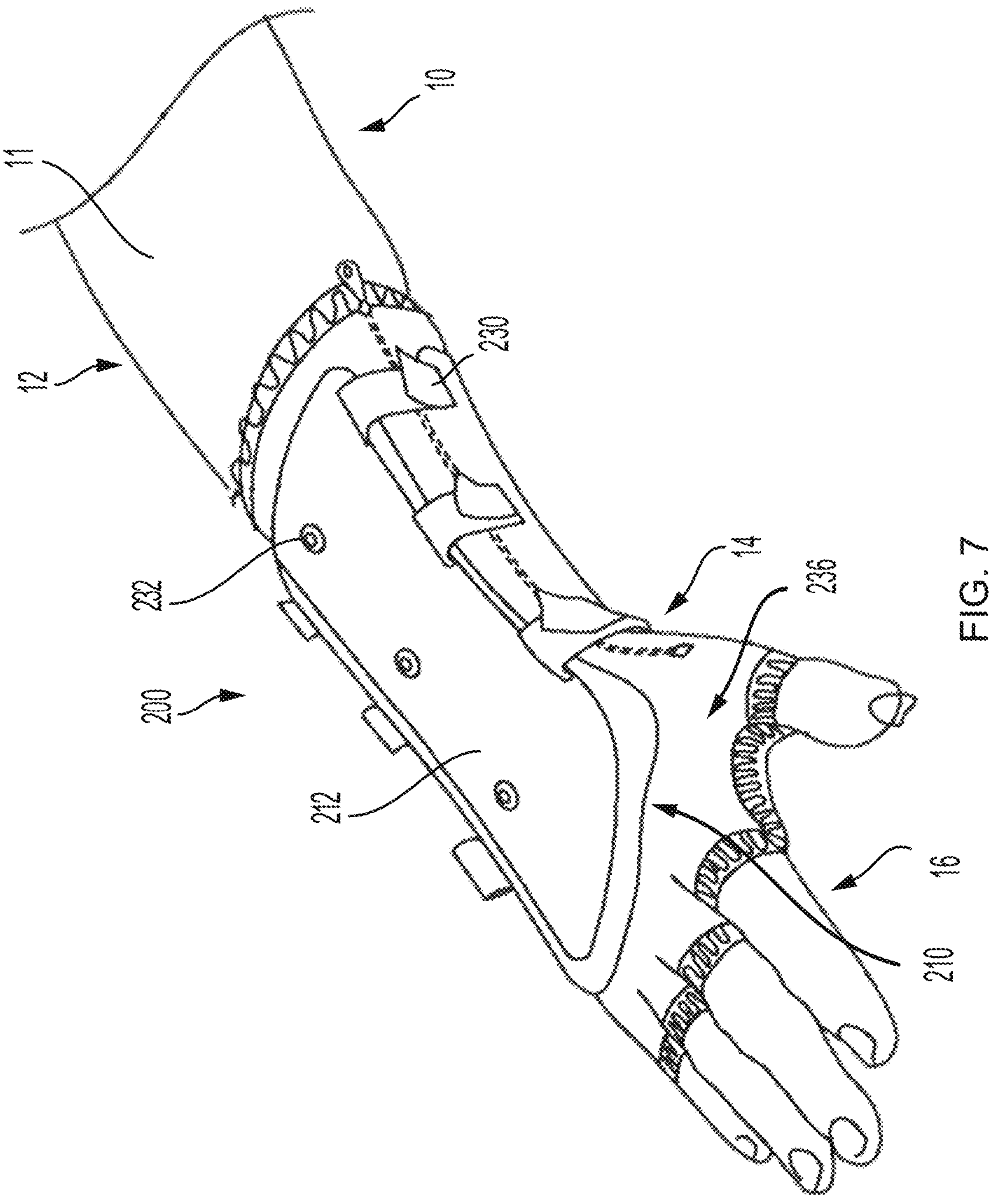
FIG. 7 is a top perspective view of a splint device for immobilizing the limb of a user in accordance with an alternate embodiment of the present invention.
Figure 8:
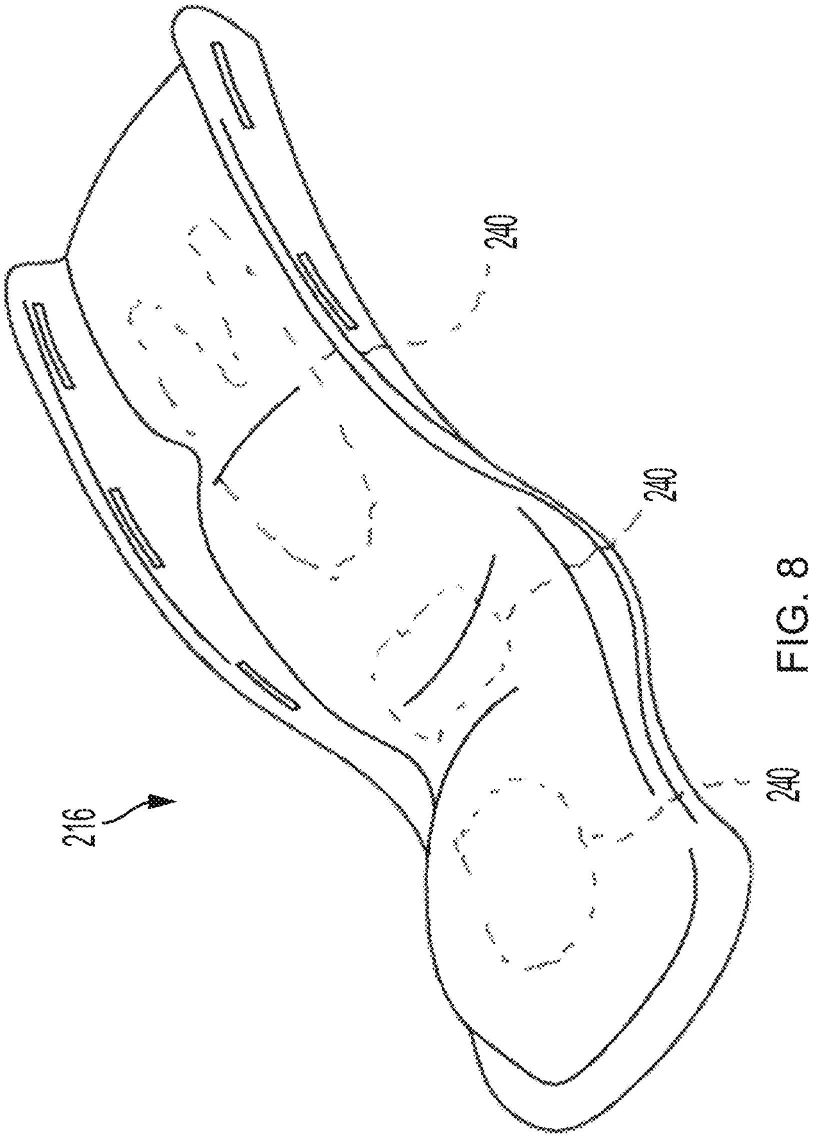
FIG. 8 is a top perspective view of the lower outer shell of the splint device shown in FIG. 7 with the plurality of inflatable bladders.
Figure 9:
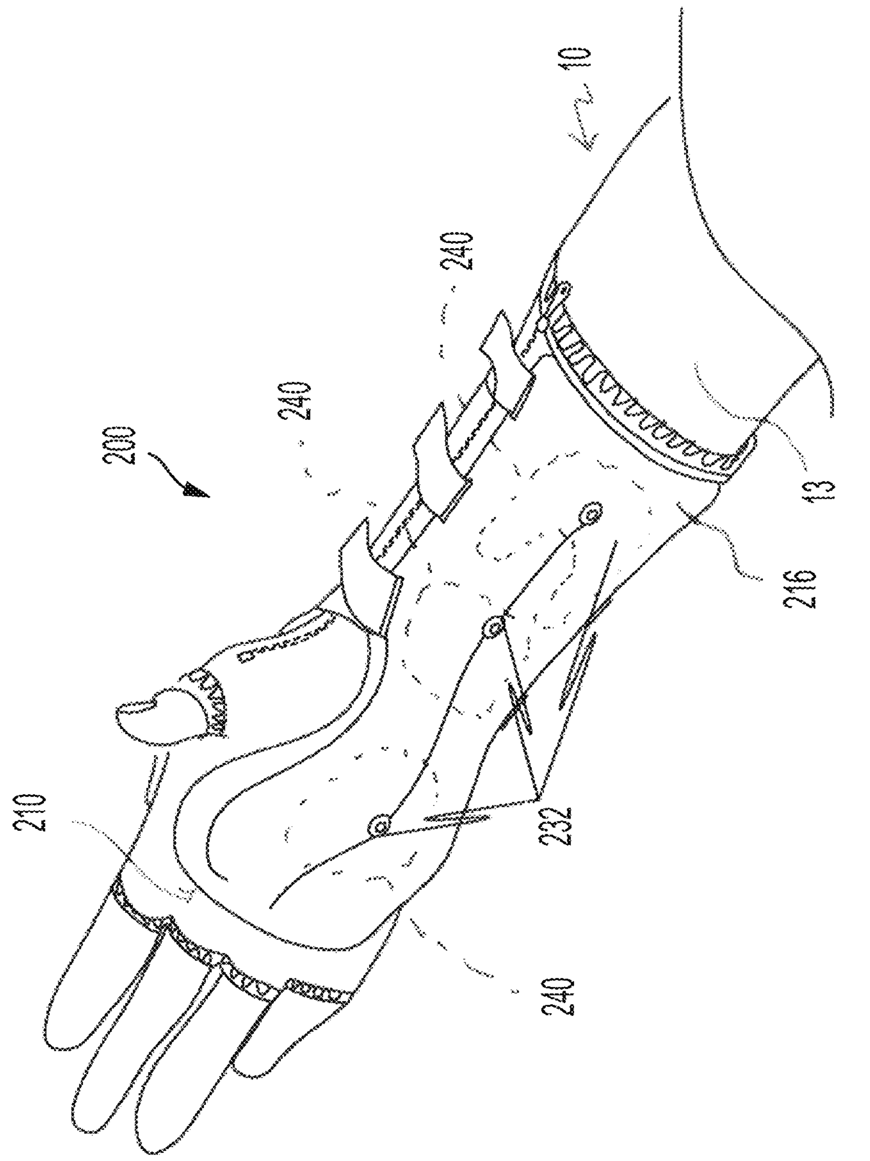
FIG. 9 is a bottom perspective view of the splint device shown in FIG. 7 or the arm of the user.

Referring now to FIGS. 7 through 9, an alternate embodiment of a splint device 200 in accordance with the invention is shown. FIG. 7 shows a top perspective view of the splint device 200 for immobilizing the arm 10 of a user. The splint device 200 may include a rigid outer shell assembly 210 and a plurality of inflatable bladders 240.

The outer shell assembly 210 may include an upper (dorsal) shell body 212 and a lower (volar) shell body 216. Preferably, the dorsal shell body 212 is configured to be positioned against a dorsal side 11 of the arm 10 of the user, and the volar shell body 216 is configured to be positioned against a volar side 13 of the arm 10 of the user. Preferably, the outer shell assembly includes at least one fastening element 230, such as an adjustable strap (e.g., an adjustable SPANDEX strap), to fasten the dorsal and volar shell bodies 212 and 216 on the user's arm 10. The dorsal shell body 212 may be fastened to the volar shell body 216 using the at least one fastening element 230 after positioning the dorsal shell body 212 on the dorsal side 11 of the arm 10 and positioning the volar shell body 216 on the volar side 13 of the arm 10 for immobilizing the hand, wrist, and forearm of the user.

Further, the plurality of inflatable bladders 240 are inflatable based on transferring at least one fluid into the plurality of inflatable bladders 240. The at least one fluid may include a gas, a liquid, etc. Preferably, multiple inflatable bladders 240 are supported within each half of the splint device 200. As shown, each half of the splint 200 includes three independently inflatable bladders 240. The plurality of inflatable bladders 240 are attached to the inner surfaces of both the dorsal shell body 212 and the volar shell body 216. Further, at least one valve 232 is disposed on the dorsal shell body 212 and the volar shell body 216 for each inflatable bladder 240 so that each inflatable air bladder 240 is inflatable independently of the other inflatable bladders 240.

Preferably, in some embodiments, the outer shell assembly 210 is constructed of a rigid material and is contoured to support the hand 16, wrist 14, and forearm 12 of the user. For example, the dorsal shell body 212 may be contoured in a first shape for receiving at least a portion of the dorsal side 11 of the user's arm 10, whereas the volar shell body 216 may be contoured in a second shape for receiving at least a portion of the volar side 13 of the arm 10 of the user, as best seen in FIG. 8.

As noted above, the outer shell assembly 210 may include at least one valve 232 disposed on the dorsal shell body 212 and the volar shell body 216. Each valve 232 may be fluidly coupled with a single one of the plurality of inflatable bladders 240. Also as noted above, the plurality of inflatable bladders 240 is inflatable based on the transferring of a fluid into the inflatable bladders 240 through the corresponding valves 232.

Further, in some embodiments, the apparatus may include a glove 236. The glove 236 is preferably constructed of a soft stretchable material. The glove 236 is preferably secured to the inner surface of the dorsal shell body 212 and the inner surface of the volar shell 216, and is worn on the lower arm 10 of the user. One or more of the plurality of inflatable bladders 240 may be disposed between the glove 236 and the outer shell assembly 210. The glove is preferably configured to receive the hand 16 of the user for properly positioning the dorsal shell body 212 against the dorsal side 11 of the arm 10 and the volar shell body 216 against the volar side 13 of the arm 10. With the glove 236 and, therefore, inflatable bladders 240 properly positioned, the corresponding inflatable bladders 240 may be inflated to supportively fill voids, contours, and gaps around the area of concern of the hand 16, wrist 14, and forearm 12.

In some embodiments, the splint device 200 may include at least one inflating device (not shown) that is configured to inflate the plurality of inflatable bladders 240 by the transferring of fluid both into and out of to the plurality of inflatable bladders 240. Further, the transferring fluid into and out of the plurality of inflatable bladders 240 may include transferring a given amount of fluid that corresponds to an amount of pressure that is designed to be exerted by the plurality of inflatable bladders 240 against the corresponding portions of the user's arm. Further, in an instance, the at least one amount of the at least one fluid in the plurality of inflatable bladders corresponds to at least one volume of the plurality of inflatable bladders.

Although the splint devices 100, 200 are shown and described herein for use on the arm 10 of a user, alternate embodiments of the splint devices may be configured for use on other portions of a user's body such as a knee, ankle, elbow, shoulder, thumb, and the like.

In exemplary aspects, the layout and configuration of each inflatable bladder of the splint devices 100, 200 may be determined and/or optimized based upon a three-dimensional scan (e.g., three-dimensional body scan, X-ray scan, computed tomography, magnetic resonance imaging, combinations thereof, and the like) of the user's affected body portion. In particular, the three-dimensional scan can be used to determine a shape, dimension(s), level of inflation, or other characteristic of each bladder that allows the bladder to fill the gaps/voids/spaces produced by the anatomical curvatures and contours of the user's body, thereby providing optimal levels of support to help reduce inflammation and pain. Optionally, a processing device 500 as disclosed herein or a remote computing device can receive the three-dimensional scan and be configured to determine one or more optimized characteristics of each bladder. In these optional aspects, it is contemplated that the processing device 500 or other computing device can be configured to provide an output to a clinician or other medical professional indicative of the optimized characteristics of each bladder. The output can optionally include an indication of particular splint device configurations that have bladders capable of providing the optimized characteristics. In further aspects, it is contemplated that the three-dimensional scan can be used to direct formation of the bladders using a liner (or a plurality of respective liners), and the bladders can then be positioned within the splint device as disclosed herein.

Figure 10:
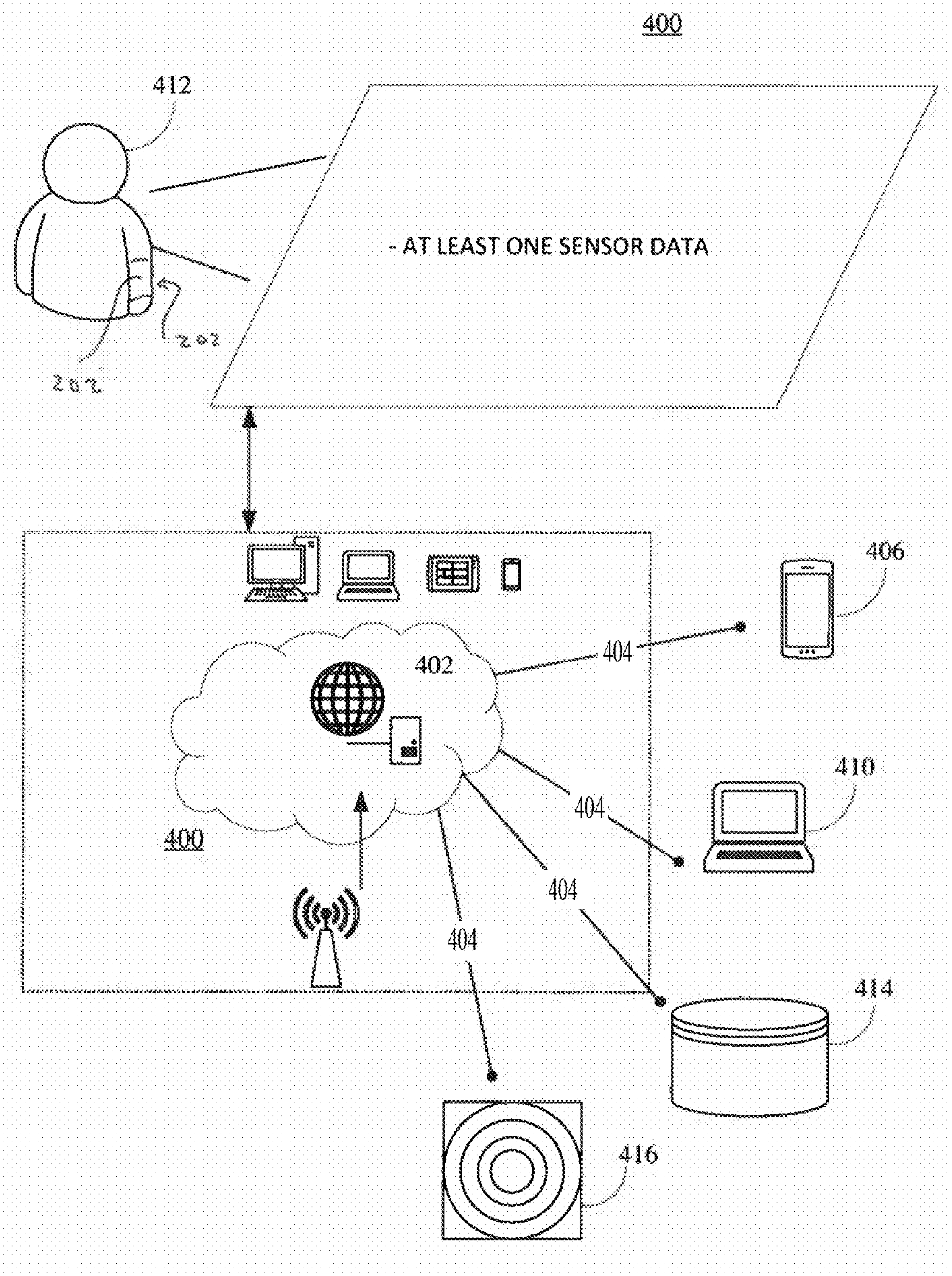
FIG. 10 is a schematic illustration of an online platform consistent with various embodiments of the present invention.
Figure 11:
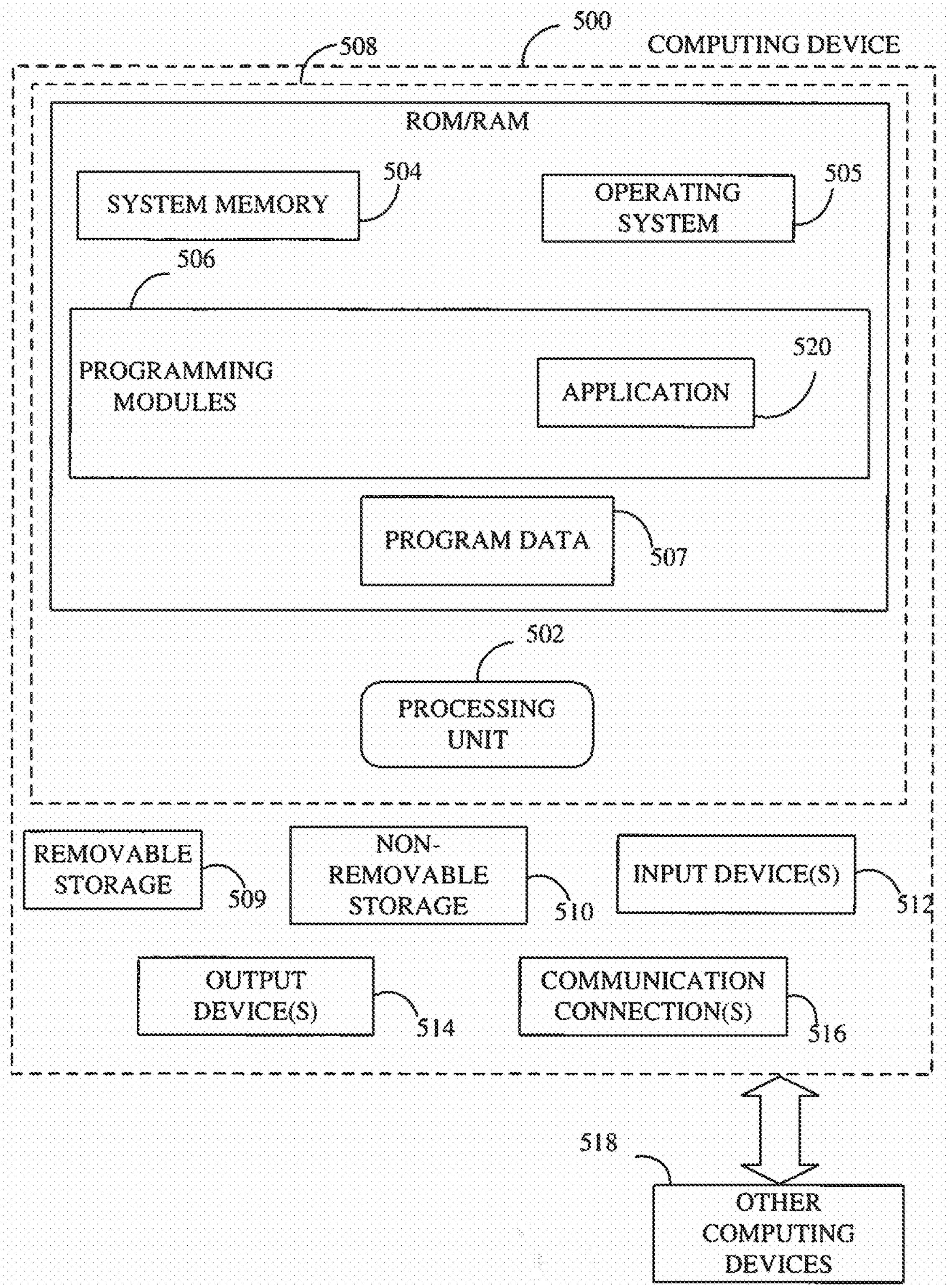
FIG. 11 is a block diagram of a computing device for implementing the methods disclosed herein, in accordance with some embodiments of the present invention.

Referring additionally to FIG. 10, embodiments of splint device 200 may include at least one sensor 202 and a processing device 500 (FIG. 11). The at least one sensor 202 may be configured for generating sensor data based on detecting a pressure exerted by at least one portion of the hand on the outer shell assembly 210. Preferably, the processing device 500 is communicatively coupled with the at least one sensor 202. Additionally, the processing device 500 can be configured to analyze the sensor data and may be configured to determine a volume of fluid for each of the plurality of inflatable bladders 240 based on the analysis of the sensor data. The processing device 500 may be configured for generating commands for the inflating device and be communicatively coupled with the at least one inflating device so that the transfer of fluid may be accomplished automatically (in response to commands from the processing device). Although not shown in a drawing, embodiments of splint device 100 may also include at least one sensor and a processing device as disclosed herein with respect to splint device 200.

FIG. 10 is an illustration of an online platform 400 consistent with various embodiments of the present disclosure. By way of non-limiting example, the online platform 400 to facilitate healing hand injuries may be hosted on a centralized server 402, such as, for example, a cloud computing service. The centralized server 402 may communicate with other network entities, such as, for example, a mobile device 406 (such as a smartphone, a laptop, a tablet computer, etc.), other electronic devices 410 (such as desktop computers, server computers, etc.), databases 414, sensors 416, actuators (not shown) and an apparatus 418 over a communication network 404, such as, but not limited to, the Internet. Further, users of the online platform 400 may include relevant parties such as, but not limited to, end-users and administrators. Accordingly, in some instances, electronic devices operated by the one or more relevant parties may be in communication with the online platform 400.

A user 412, such as the one or more relevant parties, may access the online platform 400 through a web-based software application or browser. The web-based software application may be embodied as, for example, but not be limited to, a website, a web application, a desktop application, and a mobile application compatible with a computing device 500.

With reference to FIG. 11, a system consistent with an embodiment of the disclosure may include a computing device or cloud service, such as computing device 500. In a basic configuration, computing device 500 may include at least one processing unit 502 and a system memory 504. Depending on the configuration and type of computing device, system memory 504 may comprise, but is not limited to, volatile (e.g. random-access memory (RAM)), non-volatile (e.g. read-only memory (ROM)), flash memory, or any combination. System memory 504 may include operating system 505, one or more programming modules 506, and may include a program data 507. Operating system 505, for example, may be suitable for controlling computing device 500's operation. In one embodiment, programming modules 506 may include image-processing module, machine learning module and/or image classifying module. Furthermore, embodiments of the disclosure may be practiced in conjunction with a graphics library, other operating systems, or any other application program and is not limited to any particular application or system. This basic configuration is illustrated in FIG. 6 by those components within a dashed line 508.

Computing device 500 may have additional features or functionality. For example, computing device 500 may also include additional data storage devices (removable and/or non-removable) such as, for example, magnetic disks, optical disks, or tape. Such additional storage is illustrated in FIG. 11 by a removable storage 509 and a non-removable storage 510. Computer storage media may include volatile and nonvolatile, removable and non-removable media implemented in any method or technology for storage of information, such as computer-readable instructions, data structures, program modules, or other data. System memory 504, removable storage 509, and non-removable storage 510 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 500. Any such computer storage media may be part of device 500. Computing device 500 may also have input device(s) 512 such as a keyboard, a mouse, a pen, a sound input device, a touch input device, a location sensor, a camera, a biometric sensor, etc. Output device(s) 514 such as a display, speakers, a printer, etc. may also be included. The aforementioned devices are examples and others may be used.

Computing device 500 may also contain a communication connection 516 that may allow device 500 to communicate with other computing devices 518, such as over a network in a distributed computing environment, for example, an intranet or the Internet. Communication connection 516 is one example of communication media. Communication media may typically be embodied by computer-readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 504, including operating system 505. While executing on processing unit 502, programming modules 506 (e.g., application 520 such as a media player) may perform processes including, for example, one or more stages of methods, algorithms, systems, applications, servers, databases as described above. The aforementioned process is an example, and processing unit 502 may perform other processes. Other programming modules that may be used in accordance with embodiments of the present disclosure may include sound encoding/decoding applications, machine learning application, acoustic classifiers, etc.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the foregoing invention has been described in some detail by way of illustration and example for purposes of clarity of understanding, certain changes and modifications may be practiced within the scope of the appended claims.

What is claimed is:

1. A splint for use on a forearm, a wrist, and a hand of a user, comprising:

a rigid shell assembly including a dorsal shell body and a volar shell body, the dorsal shell body and the volar shell body each including a forearm portion, a wrist portion, and a hand portion, wherein the dorsal shell body and the volar shell body are configured to releasably receive the forearm, the wrist, and the hand of the user therebetween;

a dorsal compressible assembly extending along an inner surface of the dorsal shell body, wherein the dorsal compressible assembly comprises an inflatable forearm bladder adjacent the forearm portion, an inflatable wrist bladder adjacent the wrist portion, and an inflatable hand bladder adjacent the hand portion; and a volar compressible assembly extending along an inner surface of the volar shell body, the volar compressible assembly including an inflatable forearm bladder adjacent the forearm portion, an inflatable wrist bladder adjacent the wrist portion, and an inflatable hand bladder adjacent the hand portion of the volar shell body, wherein each of the inflatable forearm bladder, the inflatable wrist bladder, and the inflatable hand bladder of the volar compressible assembly includes a respective valve to allow each of the inflatable forearm bladder, the wrist bladder, and the hand bladder to be inflated independently of the other inflatable bladders, wherein each of the inflatable forearm bladder, the inflatable wrist bladder, and the inflatable hand bladder of the dorsal compressible assembly includes a respective valve to allow each of the inflatable forearm bladder, the wrist bladder, and the hand bladder of the dorsal compressible assembly to be inflated independently of the other inflatable bladders of the dorsal compressible assembly, and wherein the dorsal compressible assembly further comprises a compressible material pad that extends along the inner surface of the volar shell body, wherein an outer surface of the compressible material pad abuts the inner surface of the dorsal shell body, and the inflatable forearm bladder, the inflatable wrist bladder, and the inflatable hand bladder are disposed on an inner surface of the compressible material pad.

2. The splint of claim 1, wherein the volar compressible assembly further comprises a second compressible material pad that extends along the inner surface of the volar shell portion.

3. The splint of claim 2, wherein an outer surface of the second compressible material pad abuts the inner surface of the volar shell body, and the inflatable forearm bladder, the inflatable wrist bladder, and the inflatable hand bladder are disposed on an inner surface of the second compressible material pad.

4. The splint of claim 2, wherein the inflatable forearm bladder, the inflatable wrist bladder, and the inflatable hand bladder are configured to be adjacent the forearm, the wrist, and the hand of the user, respectively, when the splint is applied to the user.

5. The splint of claim 2, wherein the second compressible material pad further comprises a memory foam material pad.

6. The splint of claim 1, wherein the valves extend from the inflatable forearm, the wrist, and hand bladders to an outer surface of the volar shell body.

7. The splint of claim 1, further comprising a plurality of adjustable straps, wherein the dorsal shell body and the volar shell body are secured to each other with plurality of adjustable straps.

8. The splint of claim 7, where each adjustable strap of the plurality of adjustable straps includes a hook-and-loop fastener.

9. The splint of claim 1, wherein the inflatable forearm bladder, the inflatable wrist bladder, and the inflatable hand bladder of the dorsal compressible assembly are configured to be adjacent the forearm, the wrist, and the hand of the user, respectively, when the splint is applied to the user.

10. A method of immobilizing a forearm, a wrist, and a hand of user, comprising the steps of:

positioning a splint on the user, the splint comprising:

a rigid shell assembly including a dorsal shell body and a volar shell body, the dorsal shell body and the volar shell body each including a forearm portion, a wrist portion, and a hand portion, wherein the dorsal shell body and the volar shell body are configured to releasably receive the forearm, the wrist, and the hand of the user therebetween;

a dorsal compressible assembly extending along an inner surface of the dorsal shell body, wherein the dorsal compressible assembly comprises an inflatable forearm bladder adjacent the forearm portion, an inflatable wrist bladder adjacent the wrist portion, and an inflatable hand bladder adjacent the hand portion; and a volar compressible assembly extending along an inner surface of the volar shell body, the volar compressible assembly including an inflatable forearm bladder adjacent the forearm portion, and an inflatable wrist bladder adjacent the wrist portion of the volar shell body, wherein each of the inflatable forearm bladder, the inflatable wrist bladder, and the inflatable hand bladder of the volar compressible assembly includes a respective valve to allow each of the inflatable forearm bladder, the wrist bladder, and the hand bladder to be inflated independently of the other inflatable bladders, wherein each of the inflatable forearm bladder, the inflatable wrist bladder, and the inflatable hand bladder of the dorsal compressible assembly includes a respective valve to allow each of the inflatable forearm bladder, the wrist bladder, and the hand bladder of the dorsal compressible assembly to be inflated independently of the other inflatable bladders of the dorsal compressible assembly, and wherein the dorsal compressible assembly further comprises a compressible material pad that extends along the inner surface of the volar shell body, wherein an outer surface of the compressible material pad abuts the inner surface of the dorsal shell body, and the inflatable forearm bladder, the inflatable wrist bladder, and the inflatable hand bladder are disposed on an inner surface of the compressible material pad, wherein the splint is positioned on the user so that the inflatable forearm bladder and the inflatable wrist bladder of the volar compressible assembly are adjacent the forearm and the wrist of the user, respectively;

inflating the inflatable forearm bladder to a first pressure; and inflating the inflatable wrist bladder to a second pressure, wherein the first pressure and the second pressure are not equal.

11. The method of claim 10, the method further comprising:

positioning the inflatable hand bladder of the volar compressible assembly adjacent the hand of the user; and inflating the inflatable hand bladder to a third pressure, wherein the third pressure is not equal to the first pressure and the second pressure.

12. The method of claim 11, further comprising:

providing a valve for each of the inflatable forearm bladder, the inflatable wrist bladder, and the inflatable hand bladder so that the inflatable bladders are independently inflatable.

13. The method of claim 10, further comprising:

providing a plurality of straps that adjustably secure the dorsal shell body and the volar shell body to each other.

14. A splint for use on a limb of a user, comprising:

a rigid shell assembly including a first shell body and a second shell body, wherein the first shell body and the second shell body are configured to releasably receive the limb of the user therebetween;

a first compressible assembly extending along an inner surface of the first shell body; and a second compressible assembly extending along an inner surface of the second shell body, the second compressible assembly including a first inflatable bladder and a second inflatable bladder;

wherein the first shell body is configured to receive a first side of the limb and the second shell body is configured to receive an opposite second side of the limb;

wherein each of the first inflatable bladder and the second inflatable bladder includes a valve to allow each of the first and the second inflatable bladders to be inflated independently of the other inflatable bladder, and wherein the second compressible assembly further comprises a compressible material pad that extends along the inner surface of the second shell body, and wherein an outer surface of the compressible material pad abuts the inner surface of the second shell body, and wherein the first and second bladders are disposed on an inner surface of the compressible material pad.

15. The splint of claim 14, wherein:

the first shell body includes a forearm portion and a wrist portion, and the first inflatable bladder and the second inflatable bladder further comprise an inflatable forearm bladder and an inflatable wrist bladder, respectively.

16. The splint of claim 15, wherein the inflatable forearm bladder and the inflatable wrist bladder are configured to be adjacent the forearm and the wrist of the limb of the user when the splint is applied to the limb.

17. The splint of claim 14, wherein the first compressible assembly further comprises:

a first inflatable bladder and second inflatable bladder;

wherein each of the first inflatable bladder and the second inflatable bladder of the first compressible assembly includes a respective valve to allow each of the first and the second inflatable bladders of the first compressible assembly to be inflated independently of the other of the first and second inflatable bladders of the first compressible assembly.

* * * * *